(12) United States Patent
Van Der Heide et al.

(10) Patent No.: US 9,656,933 B2
(45) Date of Patent: May 23, 2017

(54) PROCESS FOR THE CONVERSION OF SACCHARIDE-CONTAINING FEEDSTOCK

(71) Applicant: SHELL OIL COMPANY, Houston, TX (US)

(72) Inventors: Evert Van Der Heide, Amsterdam (NL); Pieter Huizenga, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 14/914,393

(22) PCT Filed: Aug. 29, 2014

(86) PCT No.: PCT/EP2014/068350
§ 371 (c)(1),
(2) Date: Feb. 25, 2016

(87) PCT Pub. No.: WO2015/028593
PCT Pub. Date: Mar. 5, 2015

(65) Prior Publication Data
US 2016/0221903 A1    Aug. 4, 2016

(30) Foreign Application Priority Data
Aug. 30, 2013   (EP) .................................... 13182406

(51) Int. Cl.
*C07C 29/60*   (2006.01)
*C07C 29/132*   (2006.01)

(52) U.S. Cl.
CPC ............ *C07C 29/60* (2013.01); *C07C 29/132* (2013.01)

(58) Field of Classification Search
CPC .............................. C07C 29/132; C07C 29/60
See application file for complete search history.

(56) References Cited

U.S. PATENT DOCUMENTS

| 5,648,579 A | 7/1997 | Kulprathipanja et al. |
| 2011/0160482 A1 | 6/2011 | Nagaki et al. |

(Continued)

FOREIGN PATENT DOCUMENTS

| CN | 102190562 | 9/2011 |
| CN | 102286548 | 12/2011 |

(Continued)

OTHER PUBLICATIONS

Liu, X. et al. "Kinetics and mechanism of thermal decomposition of corn starches with different amylose/amylopectin ratios" Starch/Stärke 2010, 62, pp. 139-146.*

(Continued)

*Primary Examiner* — Paul A Zucker
*Assistant Examiner* — Medhanit Bahta

(57) ABSTRACT

The invention provides a process for the catalytic conversion of a saccharide-containing feedstock in a reactor, wherein saccharide-containing feedstock is provided to the reactor as a feed stream through a feed pipe and is contacted with a catalyst system in the reactor, wherein the saccharide-containing feedstock in the feed pipe is maintained at a temperature below the degradation temperature of the saccharide contained therein and a section of the wall of the reactor at the point where the feed pipe enters the reactor is cooled to a temperature below the temperature of the bulk of the reactor and the reactor contents.

9 Claims, 1 Drawing Sheet

(56) References Cited

U.S. PATENT DOCUMENTS

2011/0313208 A1    12/2011    Kalnes et al.
2011/0313212 A1    12/2011    Kalnes et al.
2012/0172633 A1     7/2012    Zhang et al.

FOREIGN PATENT DOCUMENTS

CN    102643165    8/2012
CN    102675045    9/2012
WO    2013015955   1/2013

OTHER PUBLICATIONS

Liu, Yue, et al.: Tungsten Trioxide Promoted Selective Conversion of Cellulose into Propylene Glycol and Ethylene Glycol on a Ruthenium Catalyst, Renewable Resources, Angew. Chemie. Int. Ed. 2012, 51, pp. 3249-3253 Sep. 21, 2016.

Mang, Ji, et al.: Direct Catalytic Conversion of Cellulose into Ehtylene Glycol Using Nickel-Promoted Tungsten carbide Catalysts, Biomass Conversion, Angew. Chemie. Int. Ed. 2008, 47, pp. 8510-8513.

\* cited by examiner

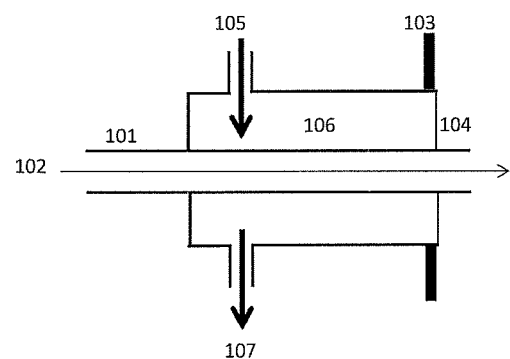

PROCESS FOR THE CONVERSION OF SACCHARIDE-CONTAINING FEEDSTOCK

PRIORITY CLAIM

The present application is a National Stage (§371) application of PCT/EP2014/068350, filed Aug. 29, 2014, which claims priority from European patent application 13182406.2 filed 30 Aug. 2013, each of which are hereby incorporated by reference in their entirety.

FIELD OF THE INVENTION

The present invention relates to a process for the catalytic conversion of a saccharide-containing feedstock.

BACKGROUND OF THE INVENTION

In recent years increasing efforts have been focused on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. An example of such a process is described in Angew. Chemie. Int. Ed. 2012, 51, 3249 and US 2011/0313212 and may be used to provide ethylene glycol and 1,2-propylene glycol, which are valuable materials with a multitude of commercial applications, e.g. as heat transfer media, antifreeze, and precursors to polymers, such as PET. Ethylene and 1,2-propylene glycols are traditionally made on an industrial scale by hydrolysis of the corresponding alkylene oxides, which are the oxidation products of ethylene and propylene, produced from fossil fuels.

A major problem encountered in the catalytic conversion of saccharides by known methods is the degradation of the saccharides in reactor feed pipes at high temperatures. Such degradation can lead to fouling and blocking of the pipes. One way to limit this problem is to supply the feed in the pipes at a lower temperature than the degradation temperature of the saccharides. The feed is, therefore, also at a lower temperature than the material in the reactor. However, degradation, fouling and blocking will still occur at the point where the feed pipes enter the reactor, due to the inevitable increase in temperature at this point.

Fouling and blocking of the feed pipes lead to reactor shut-downs for cleaning and/or replacement of the feed pipes and connections. This translates to higher running costs and reduced productivity. It would, therefore, be highly desirable to provide a method to reduce saccharide degradation in reactor feed pipes.

SUMMARY OF THE INVENTION

Accordingly, the present invention provides a process for the catalytic conversion of a saccharide-containing feedstock in a reactor, wherein saccharide-containing feedstock is provided to the reactor as a feed stream through a feed pipe and is contacted with a catalyst system in the reactor, wherein the saccharide-containing feedstock in the feed pipe is maintained at a temperature below the degradation temperature of the saccharide contained therein and a section of the wall of the reactor at the point where the feed pipe enters the reactor is cooled to a temperature below the temperature of the bulk of the reactor and the reactor contents.

BRIEF DESCRIPTION OF THE DRAWINGS

FIG. 1 is a schematic diagram showing an aspect of an exemplary, but non-limiting, embodiment of the process described herein.

DETAILED DESCRIPTION OF THE INVENTION

The present inventors have surprisingly found that saccharide degradation at the point of entry to a reactor can be significantly decreased by maintaining the temperature of the saccharide-containing feedstock in the feed pipe below the degradation temperature of the saccharide contained therein and also cooling a section of the wall of the reactor at the point where the feed pipe enters the reactor.

The process requires a saccharide-containing feedstock. Said feedstock suitably comprises at least 1 wt % saccharide in a solvent. Preferably the saccharide-containing feedstock comprises at least 2 wt %, more preferably at least 5 wt %, even more preferably at least 10 wt %, most preferably at least 20 wt % saccharide in a solvent. Suitably, the saccharide-containing feedstock contains no more than 50 wt %, preferably no more than 40 wt % saccharide in a solvent.

One or more further feed streams comprising solvent may also be added to the reactor together with the saccharide-containing feedstock, either through the same feed pipe or at a separate point in the reactor. It is envisaged that the composition and amount of the saccharide-containing feedstock, the contents of the reactor and the amount of any further feed stream added to the reactor will be coordinated such that the concentration of saccharide in the solvent in the reactor while the reaction is proceeding is at least 0.01 wt % saccharide in solvent. Preferably the concentration of saccharide in solvent in the reactor is at least 0.02 wt %. Most preferably the concentration of saccharide in solvent in the reactor is at least 0.25 wt %. It is envisaged that the composition and amount of the saccharide-containing feedstock, the contents of the reactor and the amount of any further feed stream added to the reactor will be coordinated such that the concentration of saccharide in the solvent in the reactor while the reaction is proceeding is at most 5 wt % saccharide in solvent. Preferably the concentration of saccharide in solvent in the reactor is at most 2 wt %. Most preferably the concentration of saccharide in solvent in the reactor is at most 1.5 wt %

The saccharide-containing feedstock comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof. If the saccharide-containing feedstock comprises oligosaccharides or polysaccharides, it is preferable that it is subjected to pre-treatment before being fed to the reactor in a form that can be converted to glycols when contacted with hydrogen in the reactor in the presence of a suitable catalyst system. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the saccharide-containing feedstock that is fed to the reactor, after pre-treatment if necessary, comprises one or more saccharide selected from the group consisting of glucose, sucrose and starch. Said saccharide is suitably present as a solution, a suspension or a slurry in the solvent. The solvent may be water, a $C_1$ to $C_6$ alcohol, or mixtures thereof. Preferably, the solvent is water. As well as the solvent provided in the saccharide-containing feedstock there may also be further solvent already present in the reactor and/or added to the saccharide-containing feedstock as set out above. Said solvent is also suitably water, a $C_1$ to $C_6$ alcohol, or mixtures thereof. Preferably, all solvents are the same. More preferably, all solvents comprise water. Most preferably, all solvents are water.

Any reactor type suitable for a semi-batch or continuous process, requiring a saccharide starting material to be added as a feed stream through a feed pipe, may be used in the process of the invention.

Preferably, the process of the invention is carried out as a continuous flow process, wherein a reaction product is continuously removed from the reactor.

In this embodiment, any reactor type or combination of reactors suitable for a continuous flow process in which reaction product is continuously removed from the reactor may be used for the process of the present invention. For example, suitable reactor systems include ebullated catalyst bed reactor systems, immobilized catalyst reactor systems having catalyst channels, augured reactor systems, fluidized bed reactor systems, mechanically mixed reactor systems and slurry reactor systems, also known as a three phase bubble column reactor systems, and combinations thereof.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the temperature in the reactor is above the degradation temperature of the one or more saccharides in the saccharide feedstock. Preferably, the reactor is heated to a temperature within these limits before addition of any starting material and is maintained at such a temperature until all reaction is complete.

To reduce degradation of the saccharide-containing feedstock, the temperature of the saccharide-containing feedstock in the feed pipe is suitably maintained below the degradation temperature of the saccharide contained therein. As used herein, the term degradation temperature relates to the temperature at which 1% of the saccharide present is degraded within an hour and will vary depending on the saccharides present. Preferably, the temperature of the saccharide-containing feedstock in the feed pipe is suitably maintained at least 10° C., more preferably at least 20° C., even more preferably at least 50° C., below the degradation temperature of the saccharide contained therein.

In one embodiment of the invention, it is preferred that a further source of heat is provided to the reactor, in order to maintain the temperature within the reactor. Said extra source of heat may be provided by providing extra heat to the reactor contents, for example by providing heat to a recycle stream. Alternatively, part of the solvent provided to the reactor may be provided as a separate stream to the saccharide-containing feedstock and at a higher temperature. This separate stream, which contains essentially no saccharide may then preferably be supplied to the reactor at a temperature such that the mixed temperature of the separate stream when combined with the saccharide-containing feedstock is within 10° C. of the temperature of the reactor.

In the process of the present invention, a section of the wall of the reactor at the point where the feed pipe enters the reactor is cooled to a temperature below the temperature of the bulk of the reactor and its contents. Preferably, said section of wall of the reactor is cooled to a temperature below the degradation temperature of the saccharide in the saccharide-containing feedstock. Preferably, the temperature of the section of wall of the reactor is suitably maintained at least 10° C., more preferably at least 20° C., even more preferably at least 50° C. below the degradation temperature of the saccharide in the saccharide containing feedstock.

The section of the reactor wall that is cooled is preferably of the smallest size possible to prevent degradation of the saccharide and build up of deposits. Typically, in the process of the present invention, rapid mixing and/or reaction will occur that will inherently reduce saccharide concentration and, thus, degradation, once the feedstock has entered the reactor. Suitably no more than 10% of the surface area will need to be cooled. Preferably, no more than 5%, more preferably no more than 2%, even more preferably no more than 1%, most preferably no more than 0.5% of the reactor wall will need to be cooled.

It will be clear to the skilled person that a balance should be maintained between increased efficiencies achieved by preventing saccharide degradation and maintaining the bulk of the reactor and its contents at the required reaction temperature without excessive application of heat.

The section of the wall of the reactor at the point where the feed pipe enters the reactor may be cooled by any suitable means known in the art. Preferably, the cooling is achieved using a cooling liquid, by air cooling, or by using the heat to evaporate water in order to provide low pressure steam. In one embodiment, the cooling may be integrated with the process such that the cooling is achieved using heat exchange with another stream in the process which requires heating. The pressure in the reactor must be above the vapour pressure of the solvent at the reaction temperature and is suitable at least 1 MPa, preferably at least 2 MPa, more preferably at least 3 MPa. The pressure in the reactor is suitably at most 16 MPa, preferably at most 12 MPa, more preferably at most 10 MPa, even more preferably at most 8 MPa, most preferably at most 6 MPa. Preferably, the reactor is pressurised to a pressure within these limits by addition of hydrogen before addition of any saccharide-containing feedstock. The pressure of hydrogen is maintained by addition of hydrogen as a separate feed stream throughout the process.

Preferably, the process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents, before the reaction starts.

In one embodiment of the invention, the catalytic conversion of a saccharide-containing feedstock in a reactor comprises the conversion of one or more saccharides in the presence of hydrogen and a catalyst system to ethylene glycol and 1,2-propylene glycol. In this embodiment of the invention, the catalyst system used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

The catalyst components may be heterogeneous or homogeneous with respect to the solvent or solvents present in the reactor during the process of the present invention. The catalyst components may be preloaded into the reactor or, if they are in liquid form or present as a solution or slurry in a solvent, they may be fed into the reactor as required in a continuous or discontinuous manner during the process of the present invention.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:100 to 1:10000. The weight ratio of the second active catalyst component (based on the amount of metal in said component) to sugar is suitably in the range of from 1:10 to 1:1000.

An effluent stream comprising ethylene glycol and 1,2-propylene glycol is continuously removed from the reactor. Said effluent stream may also contain water, hydrogen, unreacted saccharide, intermediates, by-products and catalyst materials. Said catalyst materials may be the result of decomposition of the catalyst system in the reactor or may be catalyst material present as part of an at least partially homogeneous catalyst system. Such catalyst materials will need to be separated from the effluent stream and optionally recycled to the reactor or a reactor feed stream.

The remaining effluent stream will then require separation and purification of the desired products. Unreacted saccharides and intermediates may be separated and recycled to the saccharide-containing feedstock. Hydrogen and water may also be separated and recycled to reactor feed streams.

Embodiments of the present invention will now be described by way of example only and with reference to the accompanying non-limiting figures.

The flow of saccharide-containing feedstock 102 is provided to a reactor through a feed pipe 101. Said feed pipe 101 enters the reactor through the reactor wall 103. A section 104 of the reactor wall is cooled by means of a heat exchanger 106. Cooling fluid 105 enters the heat exchanger 106 and is subsequently removed as heated fluid 107.

That which is claimed is:

1. A process for the catalytic conversion of a saccharide-containing feedstock in a reactor, wherein saccharide-containing feedstock is provided to the reactor as a feed stream through a feed pipe and is contacted with a catalyst system in the reactor, wherein the saccharide-containing feedstock in the feed pipe is maintained at a temperature below the degradation temperature of the saccharide contained therein and a section of the wall of the reactor at the point where the feed pipe enters the reactor is cooled to a temperature below the temperature of the bulk of the reactor and the reactor contents, wherein the section of the wall of the reactor at the point where the feed pipe enters the reactor is cooled using a cooling liquid, by air cooling, or by using the heat to evaporate water in order to provide low pressure steam.

2. A process according to claim 1, wherein the section of the wall of the reactor at the point where the feed pipe enters the reactor is cooled by heat exchange with another stream in the process.

3. A process according to claim 1, wherein the saccharide-containing feedstock in the feed pipe is maintained at a temperature at least 10° C. below the degradation temperature of the saccharide contained therein.

4. A process according to claim 1, wherein the saccharide containing feedstock is also contacted with hydrogen in the reactor.

5. A process according to claim 1, wherein the catalytic conversion of a saccharide-containing feedstock comprises the conversion of said feedstock into ethylene glycol and 1,2-propylene glycol in the presence of a catalyst system.

6. A process according to claim 5, wherein the catalyst system comprises at least two active catalytic components comprising, as a first active catalyst component, one or more transition metals selected from the group consisting of: Groups 8, 9 or 10 and mixtures thereof, with catalytic hydrogenation capabilities; and, as a second active catalyst component, one or more materials selected from the group consisting of: tungsten, molybdenum and compounds and complexes thereof.

7. A process according to claim 1, wherein the solvent comprises water.

8. A process according to claim 1, wherein the saccharide-containing feedstock comprises one or more of glucose, sucrose or starch.

9. A process according to claim 1, wherein the temperature in the reactor is in the range of from 150 to 250° C. and the pressure in the reactor is in the range of from 1 to 16 MPa.

* * * * *